(12) United States Patent
Klee et al.

(10) Patent No.: US 8,546,463 B2
(45) Date of Patent: Oct. 1, 2013

(54) DENTAL ADHESIVE COMPOSITION

(75) Inventors: Joachim E. Klee, Radolfzell (DE); Uwe Lehmann, Constance (DE)

(73) Assignee: DENTSPLY International Inc., York, PA (US)

( * ) Notice: Subject to any disclaimer, the term of this patent is extended or adjusted under 35 U.S.C. 154(b) by 161 days.

(21) Appl. No.: 12/386,022

(22) Filed: Apr. 13, 2009

(65) Prior Publication Data

US 2010/0022682 A1    Jan. 28, 2010

(30) Foreign Application Priority Data

Oct. 9, 2007  (WO) ............... PCT/EP2007/008764

(51) Int. Cl.
*A61K 6/083*  (2006.01)
*A61C 5/00*  (2006.01)

(52) U.S. Cl.
USPC .................. 523/118; 433/228.1; 106/35

(58) Field of Classification Search
USPC ...................... 523/118; 433/228.1
See application file for complete search history.

(56) References Cited

U.S. PATENT DOCUMENTS

| | | | | |
|---|---|---|---|---|
| 6,645,952 B2 * | 11/2003 | Stangel et al. | ............... | 514/112 |
| 6,812,266 B2 * | 11/2004 | Klee et al. | .................... | 522/171 |
| 7,452,925 B2 * | 11/2008 | Kanca, III | ..................... | 523/116 |
| 2004/0176496 A1 | 9/2004 | Han et al. | ..................... | 522/183 |
| 2007/0293642 A1 * | 12/2007 | Klee et al. | ..................... | 526/193 |

FOREIGN PATENT DOCUMENTS

| | | |
|---|---|---|
| EP | 1548021 A1 | 6/2005 |
| WO | 9857612 A1 | 12/1998 |
| WO | 0010478 A1 | 3/2000 |
| WO | 0030591 A1 | 6/2000 |
| WO | 03013444 A1 | 2/2003 |

\* cited by examiner

*Primary Examiner* — Tae H Yoon

(74) *Attorney, Agent, or Firm* — David A. Zdurne; Douglas J. Hura; Leana Levin

(57) ABSTRACT

Dental composition comprising an aqueous mixture containing
(i) a polymerizable acidic phosphoric acid ester monomer of the following formula (A):

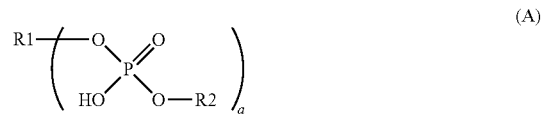

wherein
a is an integer of from 1 to 10; $R^1$ represents a hydrogen atom or a moiety of the following formula (Y)

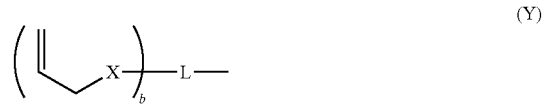

wherein X independently represent an oxygen atom, a sulfur atom, or a group NR, wherein R may be a hydrogen atom, a $C_{1-6}$ alkyl group or an acyl group; L represents an (a+b)-valent organic residue containing 1 to 20 carbon atoms and optionally including ether, thioether or amino groups or further acidic groups, whereby the carbon atoms comprise at least a+b carbon atoms selected from primary and secondary aliphatic carbon atoms, secondary alicyclic carbon atoms, and aromatic carbon atoms, each of said a+b carbon atoms linking a phosphate or 2-(oxaallyl) derivative group; b is an integer of from 1 to 10;
$R^2$ which may be the same or different, independently may be hydrogen, an allyl group or a moiety $R^1$ wherein b is 1; provided that at least one of $R^1$ and $R^2$ is not hydrogen;
(ii) one or more polymerizable N-substituted alkyl acrylic or acrylic acid amide monomers;
(iii) an organic water-miscible solvent and/or water;
(iv) a polymerization initiator;
(v) an inhibitor and/or a stabilizer;
(vi) optionally an organic or inorganic acid; and
(vii) optionally a filler and/or a fluoride releasing compound.

22 Claims, 1 Drawing Sheet

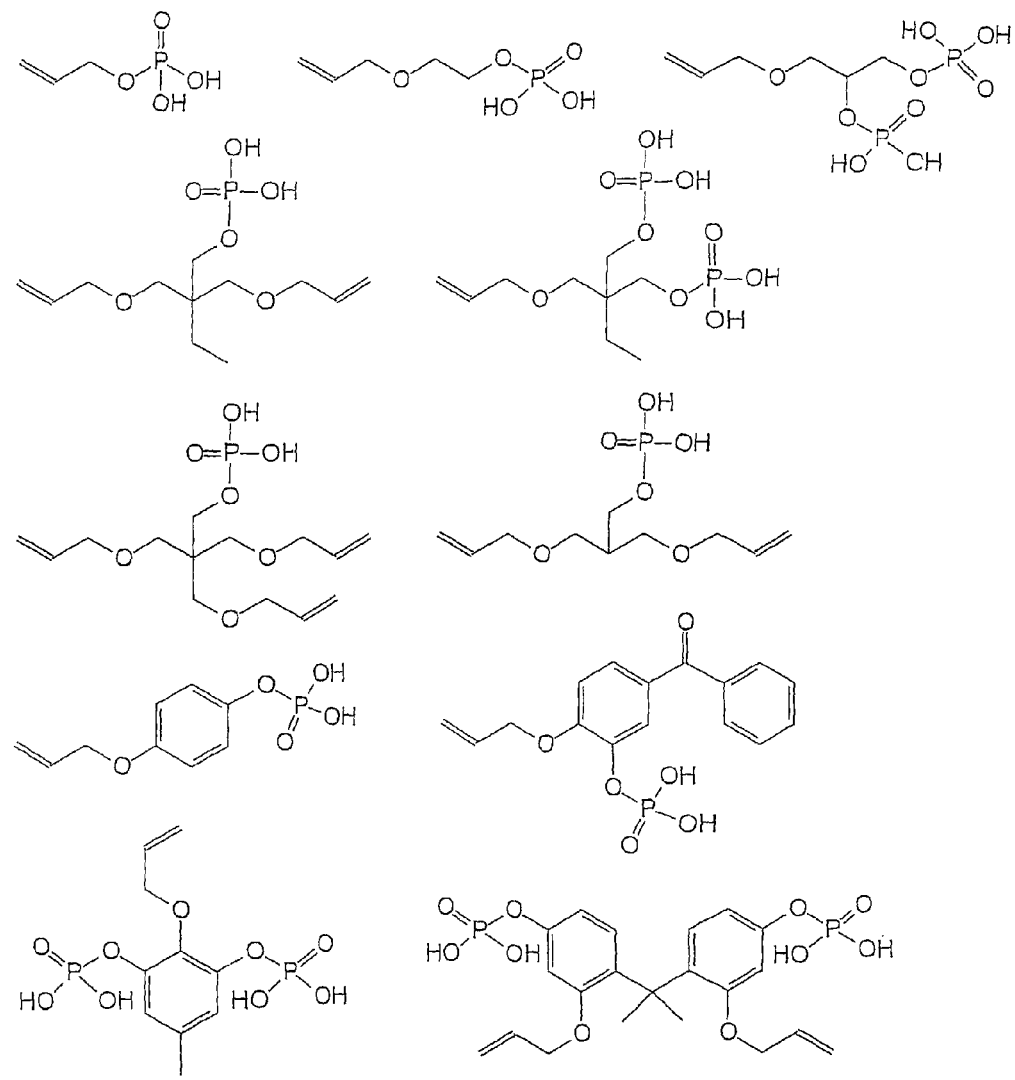

DENTAL ADHESIVE COMPOSITION

FIELD OF THE INVENTION

The present invention relates to an aqueous dental adhesive composition containing a specific polymerizable acidic phosphoric acid ester monomer. Moreover, the present invention relates to the use of the specific polymerizable acidic phosphoric acid ester monomer in an aqueous dental composition. The dental composition may be a one-part self-etching, self-priming dental adhesive. The one-part self-etching, self-priming dental adhesive may typically have a pH of at most 2. A dental composition according to the present invention provides excellent adhesion to dentin and enamel even after storage over an extended period of time.

BACKGROUND OF THE INVENTION

Aqueous dental compositions such as one-part self-etching, self-priming dental adhesive compositions are known from the prior art and typically contain a mixture of an acid, a polymerizable monomer and an initiator system in a suitable aqueous solvent. Self-etching means that the dental adhesive composition may be applied to a tooth without any preliminarily etching of enamel and dentin in a separate method step. In order to provide a self-etching feature, the composition must be acidic. Self-priming means that the dental adhesive composition may be applied to a tooth without any preliminarily application of a primer.

The acidity of the mixture must be adapted to provide sufficient etching activity on dentin and enamel surfaces. However, an increased acidity leads to a complex stability problem due to the activation of chemical bonds of the functional components of the mixture. Specifically, ester bonds present in the polymerizable monomers may be solvolysed under acid catalysis.

As a result of the stability problem of the mixture, the storage stability at room temperature of commercial one-part self-etching, self-priming dental adhesive compositions known from the prior art may be insufficient. Typical commercial one-part self-etching, self-priming dental adhesive compositions must be stored in a refrigerator in order to avoid deterioration by solvolysis or polymerization.

WO03/013444 discloses a one-part self-priming dental adhesive. WO03/013444 does not relate to dental adhesive compositions containing a polymerizable acidic phosphoric acid ester monomer.

WO98/57612 discloses composite materials and adhesion promoters. WO98/57612 does not relate to dental adhesive compositions containing polymerizable N-substituted alkyl acrylic or acrylic acid amide monomers.

WO00/30591 discloses self etching adhesive dental primer compositions and polymerizable surfactants. WO00/3059 does not relate to dental adhesive compositions containing polymerizable N-substituted alkyl acrylic or acrylic acid amide monomers.

WO00/10478 discloses adhesive compositions containing pentaerythritol triallyl ether monophosphate acid ester (PTEPAE). However, the compositions do not represent aqueous mixture and do not contain polymerizable sulfonic acid esters or polymerizable N-substituted alkyl acrylic or acrylic acid amide monomers or an organic water-miscible solvent and/or water. The compositions of WO00/10478 cannot be used as one-part self-etching, self-priming dental adhesive composition because the compositions are not aqueous mixtures. Moreover, hydrolysis stability cannot be provided by the compositions according to WO00/10478 because HEMA is always present in the compositions.

EP-A 1 548 021 discloses a one-part self-etching, self-priming dental adhesive composition having a pH of at most 2, which comprises a polymerizable acidic phosphoric acid ester monomer. However, the specific polymerizable acidic phosphoric acid ester monomers are neither disclosed nor suggested in this reference.

It is the problem of the present invention to provide an aqueous dental composition, in particular a one-part self-etching, self-priming dental adhesive composition, having a high storage stability and an excellent adhesion both to dentin and enamel.

SUMMARY OF THE INVENTION

The present invention provides an aqueous dental composition, in particular a one-part self-etching, self-priming dental adhesive, comprising an aqueous mixture containing
(i) a polymerizable acidic phosphoric acid ester monomer of the following formula (A):

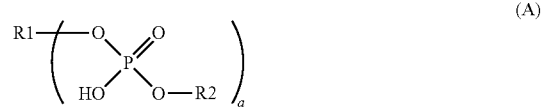

wherein
a is an integer of from 1 to 10;
$R^1$ represents a hydrogen atom or a moiety of the following formula (Y)

wherein
X independently represents an oxygen atom, a sulfur atom, or a group NR, wherein R may be a hydrogen atom, a $C_{1-6}$ alkyl group or an acyl group;
L represents an (a+b)-valent organic residue containing 1 to 20 carbon atoms and optionally including ether, thioether, amino and/or keto groups and/or further acidic groups, whereby the carbon atoms comprise at least a+b carbon atoms selected from primary and secondary aliphatic carbon atoms, secondary alicyclic carbon atoms, and aromatic carbon atoms, each of said a+b carbon atoms linking a phosphate or 2-(oxaallyl) derivative group;
b is an integer of from 1 to 10;
$R^2$ which may be the same or different, independently may be hydrogen, an allyl group or a moiety $R^1$ wherein b is 1;
provided that at least one of $R^1$ and $R^2$ is not hydrogen;
(ii) one or more polymerizable N-substituted alkyl acrylic or acrylic acid amide monomers;
(iii) an organic water-miscible solvent and/or water;
(iv) a polymerization initiator;
(v) an inhibitor and/or a stabilizer;
(vi) optionally an organic or inorganic acid; and
(vii) optionally a filler and/or a fluoride releasing compound.

The present invention furthermore provides a use of a polymerizable acidic phosphoric acid ester monomer of formula (A) as defined above in an aqueous dental composition, in particular in a one-part self-etching, self-priming dental adhesive.

BRIEF DESCRIPTION OF THE DRAWINGS

FIG. 1 shows compounds of Formula (A) which are useful in the present invention.

DETAILED DESCRIPTION OF PREFERRED EMBODIMENTS

FIG. 1 shows compounds of Formula (A) which are useful in the present invention. The aqueous dental composition, in particular a one-part self-etching, self-priming dental adhesive of the invention contains a polymerizable acidic phosphoric acid ester monomer of the following formula (A):

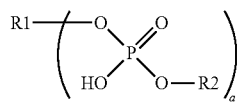
(A)

In formula A, a is an integer of from 1 to 10. Accordingly, a polymerizable acidic phosphoric acid ester monomer of formula (A) may contain up to 10 phosphoric acid ester groups. Preferably, a is in the range of from 1 to 5. More preferably, a is 1 or 2.

In formula A, $R^1$ represents a hydrogen atom or a moiety of the following formula (Y)

In formula A, $R^1$ represents a hydrogen atom or a moiety of the following formula (Y)

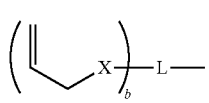
(Y)

In formula Y, X represents an oxygen atom, a sulfur atom, or a group NR, wherein R may be a hydrogen atom, a $C_{1-6}$ alkyl group or an acyl group. The acyl group may be selected from a $C_{1-18}$ alkyl carbonyl group, a $C_{1-18}$ alkenyl carbonyl group or an arylcarbonyl group, which groups may be substituted by one of more carboxylic acid or carboxylic acid ester groups. Specific examples are a acetyl group, or a (meth) acryloyl group. If more than one X is present, then the X may the same or different.

In formula Y, L represents an (a+b)-valent organic residue containing 1 to 20 carbon atoms and optionally including ether, thioether, amino and/or keto groups and/or further acidic groups, whereby the carbon atoms comprise at least a+b carbon atoms selected from primary and secondary aliphatic carbon atoms, secondary alicyclic carbon atoms, and aromatic carbon atoms, each of said a+b carbon atoms linking a phosphate or 2-(oxaallyl) derivative group. The acidic groups may be selected from phosphoric acid ester groups, sulfonic acid groups. In a preferred embodiment, L is a saturated hydrocarbon residue containing 1 to 5 carbon atoms. In a further embodiment, the (a+b)-valent organic residue represented by L contains an aromatic ring such as a phenyl ring. In a specific embodiment, $R^1$ is hydrogen. However, if $R^1$ is hydrogen, then $R^2$ cannot be hydrogen.

In formula Y, b is an integer of from 1 to 10. Accordingly, a polymerizable acidic phosphoric acid ester monomer of formula (A) may contain up to 10 allylic ester groups. Preferably, b is in the range of from 1 to 5. More preferably, b is 1, 2 or 3.

In formula Y, $R^2$ which may be the same or different, independently may be hydrogen, an allyl group or a moiety $R^1$ wherein b is 1. In a specific embodiment $R^2$ is hydrogen.

In a preferred embodiment, $R^1$ represents a hydrogen atom or a moiety of the following formula (Y')

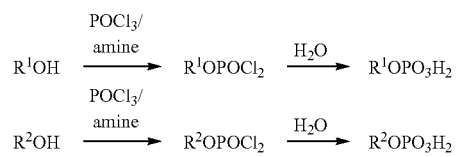
(Y')

wherein b and L are as defined for formula (Y).

In formula A, at least one of $R^1$ and $R^2$ is not hydrogen. Accordingly, a compound of formula 1 always contains at least one polymerizable moiety, preferably at least 2 polymerizable moieties.

Specific compounds useful according to the present invention are as shown in FIG. 1.

A polymerizable acidic phosphoric acid ester monomer of formula (A) wherein one of $R^1$ and $R^2$ is hydrogen may conveniently be prepared according to the following scheme:

The reaction may conveniently be carried out by dropwise addition of a solution containing phosphorous oxychloride into a solution of a suitable alcohol $R^1OH$ or $R^2OH$ and an amine at a temperature in the range of from −30 to 50° C. A suitable solvent may be selected from anhydrous solvents such as hydrocarbons, ethers or esters. Preferably the solvent is an ether. A suitable amine may be a tertiary amine such as triethylamine. The reaction may be carried out for 30 min to about 48 hours as the case requires. After the reaction, the mixture is filtered to separate any hydrochloride salt formed in the reaction. Subsequently, the mixture is poured into ice water. The mixture may be separated and the ether layer is basified with a suitable base such as sodium carbonate. Accordingly, the pH is adjusted to about 10 and subsequently lowered to about 4 by using hydrochloric acid. The organic layer is then separated and dried over a suitable drying agent such as magnesium sulphate. The desired compound of formula 1 may then be obtained by evaporation under reduced pressure.

Compounds wherein both of $R^1$ and $R^2$ are not hydrogen may be obtained by using a mixture of alcohols $R^1OH$ and $R^2OH$ or by subsequent addition of alcohols $R^1OH$ or $R^2OH$ is suitable amounts in order to provide the desired compound of formula (A).

The aqueous dental composition, in particular a one-part self-etching, self-priming dental adhesive of the invention contains polymerizable acidic phosphoric acid ester monomer of formula (A) in an amount of from 0.5 to 20 wt-%, more preferably 1.0 to 10 wt.-%.

The polymerizable acidic phosphoric acid ester monomer of formula (A) may be advantageously used in an aqueous dental composition. Preferably, the dental composition is an aqueous one-part self-etching, self-priming dental adhesive having a pH of at most 2.

The one-part self-etching, self-priming dental adhesive of the invention may preferably contain a polymerisable acidic monomer of the following formula (B):

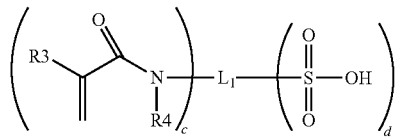

In formula (B), $R^3$ and $R^4$ independently represent a hydrogen atom, a $C_{1-18}$ alkyl group, an optionally substituted $C_{3-8}$cycloalkyl group, an optionally substituted $C_{4-18}$ aryl or heteroaryl group, an optionally substituted $C_{5-18}$ alkylaryl or alkylheteroaryl group, or an optionally substituted $C_{7-30}$ aralkyl group, whereby $R^1$ and $R^2$ may form together with the adjacent nitrogen and carbon atoms to which they are bound a 6- to 9-membered heterocyclic ring which may contain further nitrogen or oxygen atoms, and whereby the optionally substituted groups may be substituted by 1 to 5 $C_{1-5}$ alkyl group(s). Preferably, $R^3$ and $R^4$ independently represent a hydrogen atom or a $C_{1-6}$ alkyl group.

In formula (B), $L_1$ represents a (c+d) valent organic residue containing 2 to 45 carbon atoms and optionally heteroatoms such as oxygen, nitrogen and sulfur atoms, the carbon atoms including c+d carbon atoms selected from primary and secondary aliphatic carbon atoms, secondary alicyclic carbon atoms, and aromatic carbon atoms, each of said c+d carbon atoms linking a sulphonate or optionally substituted acrylamido derivative group. In a preferred embodiment, $L_1$ represents a (c+d) valent saturated-hydrocarbon residue containing 2 to 10 carbon atoms and optionally heteroatoms such as oxygen, nitrogen and sulfur atoms.

In formula (B), c and d independently represent an integer of from 1 to 10. In a preferred embodiment, c is 1 or 2. In a further preferred embodiment, d is 1 or 2.

An acidic polymerizable monomer of formula (B) may be one of the following formulas:

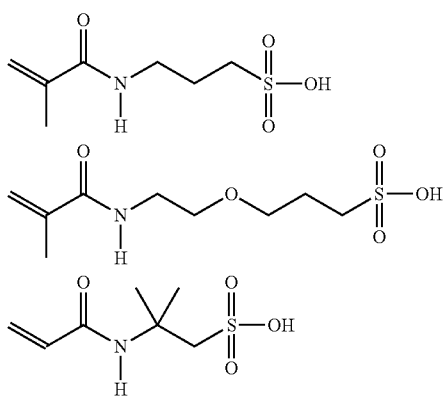

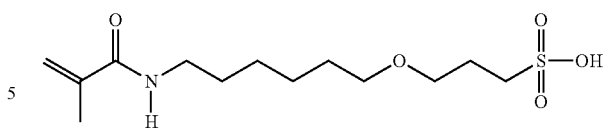

The one-part self-etching, self-priming dental adhesive of the invention may contains the polymerisable acidic monomer of formula (B) in an amount of from 0.5 to 20 wt-%, more preferably 1.0 to 10 wt. %.

The aqueous dental composition, in particular a one-part self-etching, self-priming dental adhesive of the invention further contains one or more polymerizable N-substituted alkyl acrylic or acrylic acid amide monomers. The one or more polymerizable N-substituted alkyl acrylic or acrylic acid amide monomers of component (iii) may be a compound of the one of the following formulas:

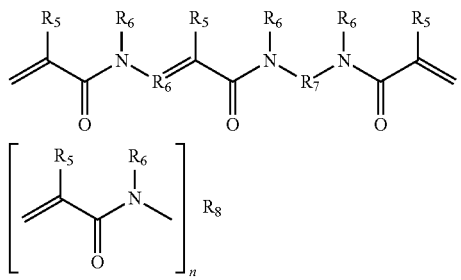

In the above formulas, $R_5$ and $R_6$ independently represent a hydrogen atom or a substituted a $C_1$ to $C_{18}$ alkyl group, an optionally substituted $C_{3-18}$ cycloalkyl group, an optionally substituted $C_{5-18}$ aryl or heteroaryl group, an optionally substituted $C_{5-18}$ alkylaryl or alkylheteroaryl group, an optionally substituted $C_{7-30}$ aralkyl group. Preferably, $R_5$ and $R_6$ independently represent a hydrogen atom or a $C_1$ to $C_8$ alkyl group.

$R_7$ represents a divalent substituted or unsubstituted organic residue having from 1 to 45 carbon atoms, whereby said organic residue may contain from 1 to 14 oxygen and/or nitrogen atoms and is selected from a $C_1$ to $C_{18}$ alkylene group wherein from 1 to 6 —$CH_2$— groups may be replaced by a —N—(C=O)—$CR_9$=$CH_2$ group wherein $R_9$ is a hydrogen atom or a $C_1$ to $C_{18}$ alkyl group, a divalent substituted or unsubstituted $C_3$ to $C_{18}$ cycloalkyl or cycloalkylene group, a divalent substituted or unsubstituted $C_4$ to $C_{18}$ aryl or heteroaryl group, a divalent substituted or unsubstituted $C_5$ to $C_{18}$ alkylaryl or alkylheteroaryl group, a divalent substituted or unsubstituted $C_7$ to $C_{30}$ aralkyl group, and a divalent substituted or unsubstituted $C_2$ to $C_{45}$ mono-, di- or polyether group having from 1 to 14 oxygen atoms. Preferably, $R_7$ represents a divalent substituted or unsubstituted organic residue having from 1 to 11 carbon atoms, whereby said organic residue may contain from 1 to 3 oxygen and/or nitrogen atoms;

$R_8$ represents a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms. Preferably, $R_8$ represents a saturated at least trivalent substituted or unsubstituted $C_1$ to $C_8$ hydrocarbon group, a saturated at least trivalent substituted or unsubstituted cyclic $C_3$ to $C_8$ hydrocarbon group, and n is at least 3.

In the above formulas, n is an integer.

Preferably, the polymerizable N-substituted alkyl acrylic or acrylic acid amide monomer may be a compound of the following formula:

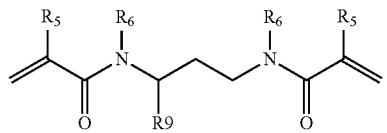

wherein $R_5$, $R_6$ and $R_9$ independently represent a hydrogen atom or a $C_1$ to $C_8$ alkyl group. Preferably, 1,3-bisacrylamido propane (BAP) or 1,3-Bisacrylamido pentane (BAPEN) may be used. Further specific examples of the polymerizable N-substituted alkyl acrylic or acrylic acid amide monomer are as follows:

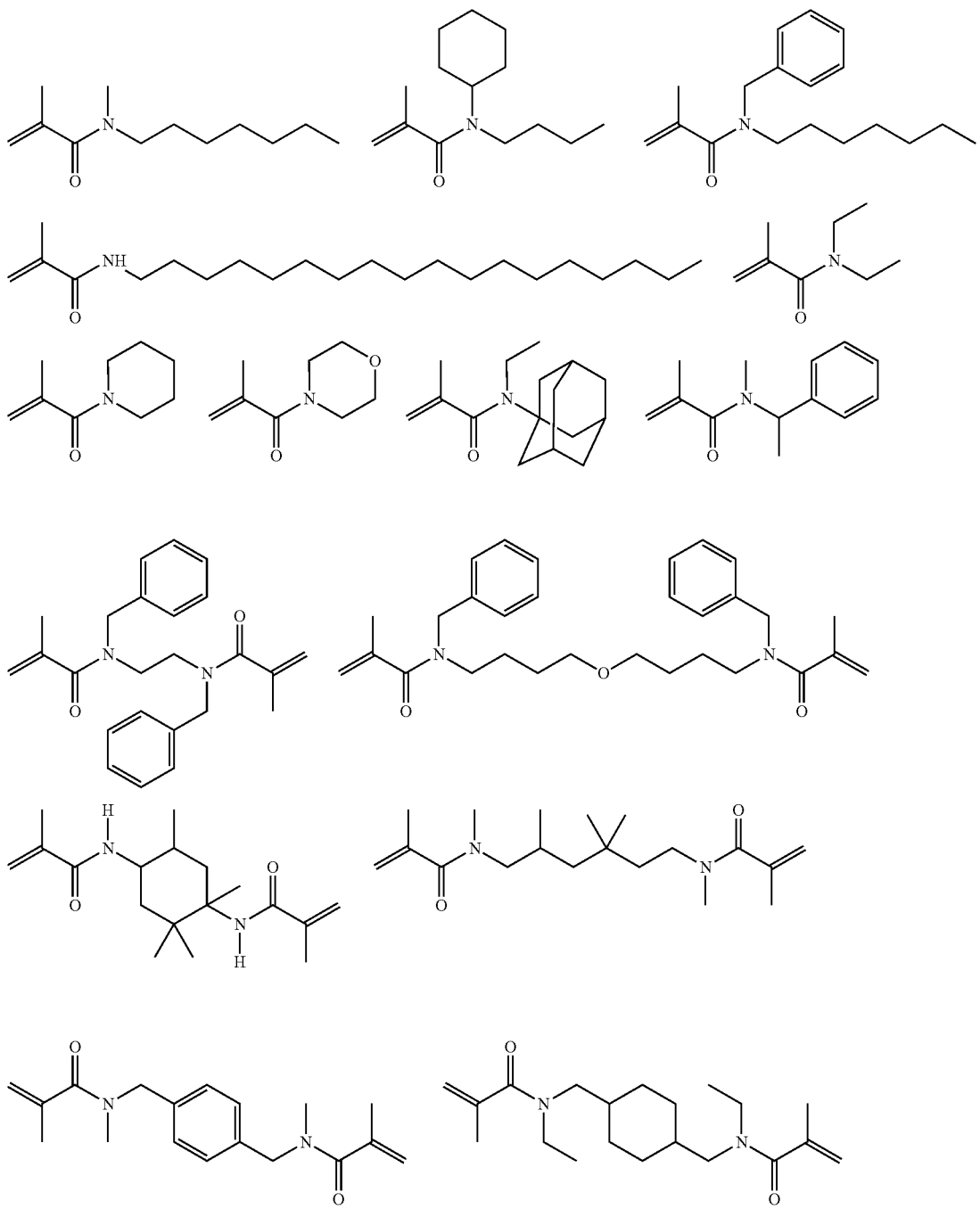

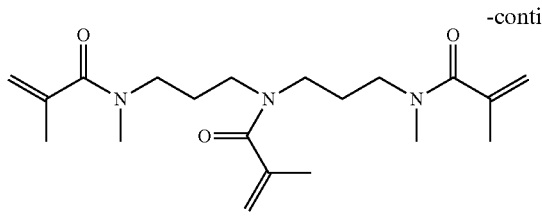
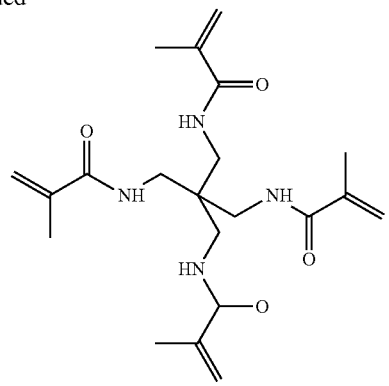
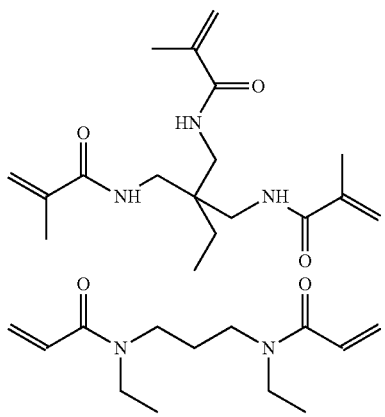
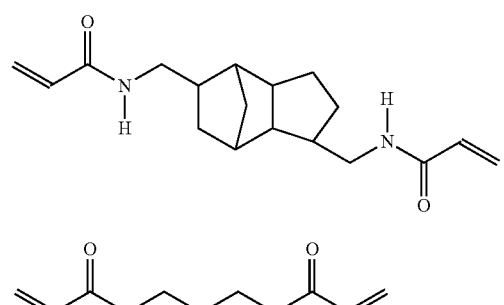

Preferably, a polymerizable N-substituted alkyl acrylic or acrylic acid amide monomer has a molecular weight of at most 400, more preferably at most 300.

The aqueous dental composition, in particular a one-part self-etching, self-priming dental adhesive of the invention may contain the one or more polymerizable N-substituted alkyl acrylic or acrylic acid amide monomers in an amount of from 10 to 70 wt-%, more preferably 15 to 40 wt-% based on the total adhesive composition.

The aqueous dental composition, in particular a one-part self-etching, self-priming dental adhesive of the invention may contain polymerizable monomers in an amount of from 5 to 90 wt-%, preferably in an amount of from 20 to 70 wt. % based on the entire composition.

The aqueous dental composition, in particular a one-part self-etching, self-priming dental adhesive of the invention is an aqueous mixture. Besides water, the adhesive may further contain an organic water-miscible solvent. Organic water-miscible solvents may be selected from the group of alcohols and ketones such as ethanol, propanol, butanol, acetone, methyl ethyl ketone.

The aqueous dental composition, in particular a one-part self-etching, self-priming dental adhesive of the invention further contains a polymerization initiator. The polymerization initiator may be a thermal initiator, a redox-initiator or a photo initiator. The photo initiator may be camphor quinine/amine and/or an acylphosphine oxide. Preferably, the initiator comprises camphor quinone.

The aqueous dental composition, in particular a one-part self-etching, self-priming dental adhesive of the invention may optionally contain an organic or inorganic acid. A suitable organic acid is a carboxylic acid which may be selected from the group of mono- or polycarboxylic acids. Specifically, the mono- or polycarboxylic acids are selected from the group of acrylic acid, methacrylic acid, fumaric acid, maleic acid, itaconic acid, and mixtures thereof. The organic acid may be present in an amount of from 3 to 20 wt. %, more preferably 5 to 15 wt. %, based on the dental adhesive composition. An inorganic acid may be incorporated into the adhesive of the present invention whereby the pH of the adhesive may be easily adjusted. Examples of suitable inorganic acids are sulfuric acid, phosphoric acid, hydrochloric acid and the like.

The aqueous dental composition, in particular a one-part self-etching, self-priming dental adhesive of the invention may optionally contain an inhibitor and/or a stabilizer. The inhibitor and/or stabilizer may be selected from hydroquinone, hydroquinone monomethyl ether, ditert. butyl cresol, tert. butyl hydroquinone. Preferably, the inhibitor and/or stabilizer is contained in the adhesive of the present invention in an amount of from 0.01 to 0.5 mol %, more preferably in an amount of from 0.05 to 0.3 mol %.

The aqueous dental composition, in particular a one-part self-etching, self-priming dental adhesive of the invention may optionally contain a filler and/or a fluoride releasing compound. The filler may be an organic or inorganic particulate filler having an average particle size in the range of from 100 nm to 10 μm. In a specific embodiment, the dental adhesive composition may further comprise a nanofiller having an average particle size in the range of from 1 to 100 nm, preferably 1 to 10 nm. The filler may contain fluoride ions which can leach from the cured composition. Furthermore, a fluoride releasing compound may also be present. Examples of the fluoride releasing compounds are inorganic salts such as fluorides of calcium, strontium and the like.

The aqueous dental composition, in particular a one-part self-etching, self-priming dental adhesive of the invention may have a pH of at most 5. Preferably, the pH is in the range of from 0.1 to 2, more preferably 0.5 to 1.5. If the pH is above 2, then the hydrolysis stability of the a polymerizable acidic phosphoric acid ester monomer decreases until to a pH of about 4 whereby the shelf-life of the adhesive is deteriorated. Moreover, if the pH of the composition is increased above 2, then the composition cannot be successfully used as a dental adhesive without an additional etching composition. Preferably, the composition is stable at storage for at least 10 days at 60° C.

The aqueous dental composition is preferably a one-part self-etching, self-priming dental adhesive.

Preferably, the dental adhesive according to the invention provides an adhesion to enamel and dentin of at least 10 MPa, preferably at least 15 MPa. In a preferred embodiment, the dental composition of the invention is a hydrolysis stable one-part self-etching, self-priming dental adhesive composition. In particular the dental composition is hydrolysis stable for at least one 10 days at a storage temperature of 60° C., whereby after such storage the bond strength of an adhesive prepared from such a dental composition to enamel and/or dentin is at least 10 MPa.

A one-part composition means that the composition of the present invention is contained in only one container which may be stored and allows application of the composition without any mixing and without any special equipment before the application.

The invention will now be further illustrated by the following examples and comparative examples.

Preparative Example 1

Pentaerythritol triallyl ether monophosphate PETAP

To a solution of 9.909 g pentaerythritol triallyl ether (70%) and 3.809 triethylamine in 60 ml dry diethyl ether a solution of 5.30 g phosphor oxychloride in 60 ml dry diethylether was added under stirring over a time range of 55 min, so that the temperature of the reaction mixture stayed between −5 and 0° C. After the addition was finished the suspension was stirred for additional 23 h at room temperature.

The triethylamine hydrochloride precipitate was filtered off and the resulting solution was added over a time range of 1 h to 100 ml water under stirring, while keeping the temperature at 0-5° C. After separation from the aqueous layer the organic layer was successively washed with 100 ml of an aqueous sodium carbonate solution (25%) and 100 ml of a 1 n aqueous hydrochloride solution. The organic fraction was separated. The acidic aqueous solution was washed with 2×50 ml diethyl ether. The organic fractions were joined and dried for 0.5 h over magnesium sulfate. After filtration the solution was stabilized by the addition of 12 mg BHT. The solvents was evaporated at the rotational evaporator and dried under vacuum for 4 h at <0.1 mbar. This afforded 9.642 g of slightly yellowish, low viscose oil.

($C_{14}H_{25}O_7P$), 336.32
$n_{20}{}^D$=1.4690
$\eta_{23°\,C.}$=250.6±82.1 mPa*s
IR (film, cm$^{-1}$) 24864 ($CH_2$), 1477/1423/1308 ($CH_2$), 1087 ($CH_2OCH_2$), 994 (P=O)
$^1$H-NMR (250 MHz, DMSO, ppm) 3.40-3.34 (m), 4.17-3.80 (m), 5.25-5.10 (m); 5.89-5.77 (m).

Preparative Example 2

7-dihydrogen phosphoryl-4,7-dioxa hept-1-ene (AOEP)

To a stirred solution of 75.543 g (0.490 mol) phosphorus oxy trichloride in 250 ml diethyl ether a solution of 50.002 g (0.490 mol) 2-Allyloxyethanol and 49.590 g (0.490 mol) triethylamine in 150 ml diethyl ether was added drop wise over a time range of 90 min, while the temperature was kept at 0 to −5° C. Thereafter the reaction mixture was stirred for 16 h at 23° C. before filtration. Then the solution was added drop wise to water, while the temperature was kept at 0° C. After the addition was finished the solution was stirred for additional 0.5 h at 0° C. The layers were separated and the aqueous fraction was washed once with 150 ml diethyl ether. The product of the water phase was dissolved in 50 ml acetone and dried over Na2SO4 for 16 hours. After filtration 0.053 g (0.05 mol-%) BHT was added. Then the solvent was removed resulting in a slightly yellowish solid.

($C_5H_{11}O_5P$), 182.11 g/mol
Yield: 62.0 g (69.5% of Th)
$n_{20}{}^D$=1.4570
$\eta_{23°\,C.}$=745.2±31.2 mPa*s
IR(film, cm-1) 2868 ($CH_2$), 2326 (POH), 1646 (C=C), 1457 ($CH_2$), 975 (P=O)
$^1$H-NMR (250 MHz, CDCl$_3$, ppm) 3.63 (s, 2H, $CH_2OP$), 3.99-4.08 (d, 4H, $CH_2O$), 5.12-5.81 (m, 3H, $CH_2$=CH), 10.53 (s, 2H, OP(OH)$_2$).
$^{13}$C-NMR (63 MHz, CDCl$_3$, ppm) 133.5 (2), 1118.6 (1), 72.1 (3), 68.8 (4), 66.1 (5)

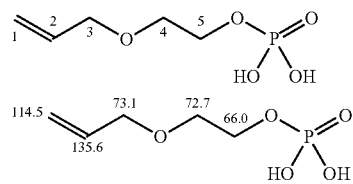

Preparative Example 3

3,3-Bis(allyloxymethyl)-5-dihydrogen phosphoryl-5-oxa pentane (TMPDAP)

To a stirred solution of 35.775 g (0.233 mol) phosphorus oxytrichloride in 250 ml diethyl ether a solution of 50.000 g (0.233 mol) 2,2-Bis(allyloxymethyl)-1-butanol and 23.609 g (0.233 mol) triethylamine in 150 ml diethyl ether was added drop wise over a time range of 90 min, while the temperature was kept at 0 to −5° C. Thereafter the reaction mixture was stirred for 16 h at 23° C. before filtration. Then the solution was added drop wise to water, while the temperature was kept at 0° C. After the addition was finished the solution was stirred for additional 0.5 h at 0° C. The layers were separated and the aqueous fraction was washed once with 150 ml diethyl ether. The organic phase was dried over Na$_2$SO$_4$ for 16 hours. After filtration 0.051 g (0.05 mol-%) BHT were added. Then the solvent was removed resulting in a slightly yellowish solid.

($C_{12}H_{23}O_6P$), 294.28 g/mol
Yield: 63.8 g (92.9% of Th)
$n_{20}{}^D$=1.4638
$\eta_{23°\,C.}$=858.8±47.6 mPa*s
IR(film, cm-1) 2864 (CH2), 2358 (POH), 1646 (C=C), 1465 (CH2), 1024 (CH2O), 924 (P=O)
1H-NMR (250 MHz, CDCl3, ppm) 0.82 (s, 3H, CH3), 1.40 (s, 2H, CH2), 3.28-3.30 (d, 2H, CH2OPO3H2), 3.91-3.92 (d, 4H, CCH2O, OCH2CH=), 5.07-5.23 (m, 2H, CH2=), 5.81-5.82 (d, 1H, CH=), 10.21-10.33 (OP(OH)2)
13C-NMR (63 MHz, CDCl3, ppm) 134.2 (2), 116.3 (1), 71.8 (3), 69.1 (4), 65.5 (8), 42.5 (5), 21.7 (6), 6.9 (7)

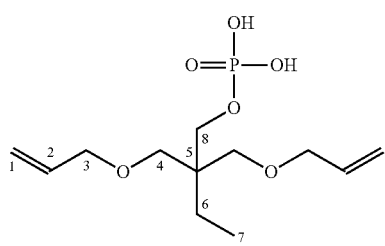 [SMILES: C=CCOCC(CC)(COCC=C)COP(=O)(O)O]

Preparative Example 3

2-(Allyloxyethyl)-2-ethyl-2-bis-[3-dihydrogen phosphoryl-3-oxa propane] (TMPADP)

To a stirred solution of 88.000 g (0.574 mol) phosphorus oxytrichloride in 250 ml diethyl ether a solution of 50.000 g (0.574 mol) 2-(Allyloxymethyl)-2-ethyl-1,3-propane diolbutanol and 58.075 g (0.574 mol) triethylamine in 150 ml of diethyl ether was added drop wise over a time range of 90 min, while the temperature was kept at 0 to −5° C. Thereafter the reaction mixture was stirred for 16 h at 23° C. before filtration. Then the solution was added drop wise to water, while the temperature was kept at 0° C. After the addition was finished the solution was stirred for additional 0.5 h at 0° C. The layers were separated and the aqueous fraction was washed once with 150 ml diethyl ether.

The product of the water phase was dissolved in 50 ml acetone and dried over $Na_2SO_4$ for 1 hour. After filtration 0.095 g (0.05 mol-%) BHT were added. Then the solvent was removed resulting in a slightly yellowish solid.

($C_9H_{20}O_9P_2$), 334.20 g/mol
Yield: 30.4 g (63.4% of Th)
$n_{20}^D$=1.4040
$\eta_{23°C}$=241.4±63.9 mPa*s
IR (film, cm−1) 2829 (CH2), 2336 (POH), 1632 (C=C), 1457 (CH2), 981 (P=O)
$^{13}$C-NMR (63 MHz, D2O, ppm) 133.6 (2), 117.2 (1), 74.3 (3), 71.9 (4), 66.5 (8), 38.9 (5), 22.2 (6), 7.2 (7)

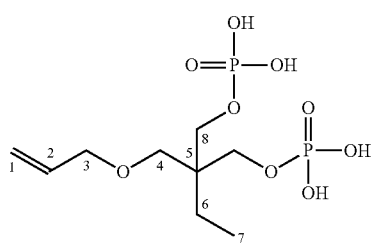 [SMILES: C=CCOCC(CC)(COP(=O)(O)O)COP(=O)(O)O]

Example 1

Using PETAP the following formulation was prepared by dissolving the monomers in a solvent mixture composed of ethanol and water:

| Example 1 | wt-% |
|---|---|
| N,N'-Bisacrylamido-1,3-propane | 26.4 |
| 3,(4),8,(9)-bis(acrylamido methyl) tricyclo-5.2.1.0 2,6 decane | 20.6 |

-continued

| Example 1 | wt-% |
|---|---|
| Pentaerythritol triallyl ether monophosphate | 3.0 |
| 2-Acrylamido-2-methyl-propane-sulfonic acid | 2.4 |
| Camphor quinone | 0.5 |
| Bis (2,4,6-trimethylbenzoyl)-phenyl phosphine oxide | 1.4 |
| Dimethylamino benzoic acid ethyl ester | 0.6 |
| Ethanol | 29.3 |
| Water | 15.8 |

The following procedure was applied for adhesion measurement to enamel and dentin:
teeth were abraded by 200 and 500 grit abrasive paper
teeth were stored at 37° C. in water
treatment with resin formulation: 20 sec
evaporation by air stream 5 sec
light curing 10 sec
Spectrum TPH (Dentsply) body cured on tooth 3 times for 20 sec
Prepared tooth were stored in water at 37° C. for 24 h and thermocycled for 1800 cycles between 5 and 55° C. before the measurement.

Under these conditions the following adhesion was determined:
Enamel: 19.4±3.9 MPa,
Dentin: 16.7±5.3 MPa.

As a result it is found that a composition of the invention provides strong adhesion to enamel and dentin without prior etching.

Application Example 2

Using AOEP of preparative example 2 in a similar formulation to application example 1 in which as solvents water, t-butanol and acrylic acid were applied the following adhesion values were measure according the procedure described above:
Enamel: 15.1±2.2 MPa
Dentin: 18.2±2.4 MPa Application Example 3

Using TMPDAP of preparative example 3 in a similar formulation to application example 1 in which as solvents water, t-butanol and acrylic acid were applied the following adhesion values were measure according the procedure described above:
Enamel: 15.0±2.5 MPa
Dentin: 20.0±3.3 MPa.

Comparative Example 1

A comparative formulation was prepared, using N-Butyl-N-(ethylphosphonic acid) acrylamid, by dissolving the monomers in a solvent mixture composed of ethanol and water:

| Comparative Example 1 | wt-% |
|---|---|
| N,N'-Bisacrylamido-1,3-propane | 264 |
| 3,(4),8,(9)-bis(acrylamido methyl) tricyclo-5.2.1.0 2,6 decane | 207 |
| N-Butyl-N-(ethylphosphonic acid) acrylamide | 30 |
| 2-Acrylamido-2-methyl-propane-sulfonic acid | 24 |
| Camphor quinone | 5 |
| Bis (2,4,6-trimethylbenzoyl)-phenyl phosphine oxide | 13 |

-continued

| Comparative Example 1 | wt-% |
|---|---|
| Dimethylamino benzoic acid ethyl ester | 6 |
| Ethanol | 293 |
| Water | 158 |

Under the same conditions as described in Example 1 the formulation was used for adhesion measurement. Under these conditions the following adhesion was determined:

Enamel: 9.4±3.0 MPa,

Dentin: 19.4±1.8 MPa.

The invention claimed is:

1. Dental composition comprising
   (i) a polymerizable acidic phosphoric acid ester monomer being characterized by one of the following formulas:

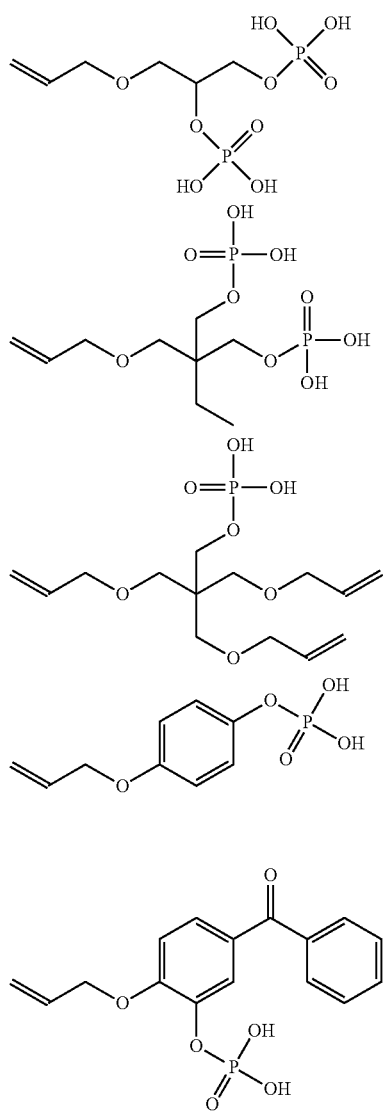

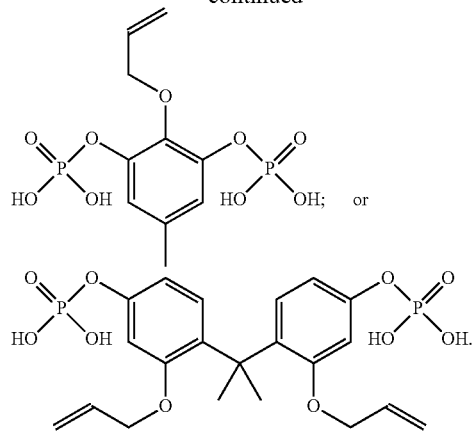

(ii) one or more polymerizable N-substituted alkyl acrylic or acrylic acid amide monomers different from the polymerizable acidic phosphoric acid ester monomer;
(iii) an organic water-miscible solvent and/or water;
(iv) a polymerization initiator;
(v) an inhibitor and/or a stabilizer;
(vi) optionally an organic or inorganic acid; and
(vii) optionally a filler and/or a fluoride releasing compound.

2. The composition according to claim 1, wherein polymerizable acidic phosphoric acid ester monomer of component (i) is characterized by one of the following formulas:

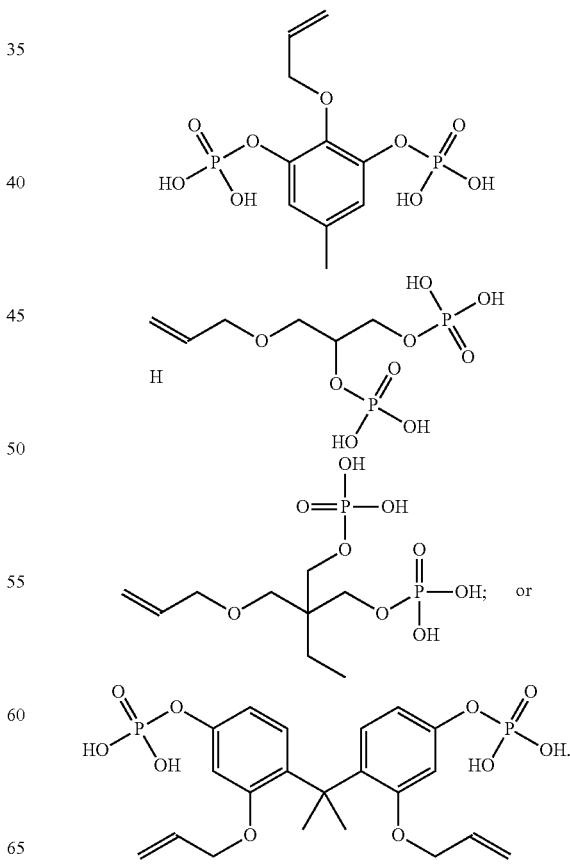

3. The composition according to claim 1, wherein polymerizable acidic phosphoric acid ester monomer of component (i) is characterized by one of the following formulas:

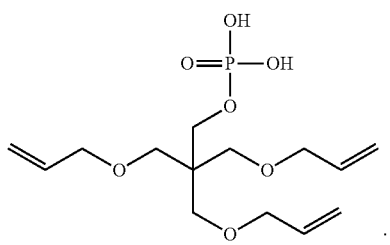 [SMILES: C=CCOCC(COCC=C)(COCC=C)COP(=O)(O)O]

4. The composition according to claim 1, wherein polymerizable acidic phosphoric acid ester monomer of component (i) is characterized by one of the following formulas:

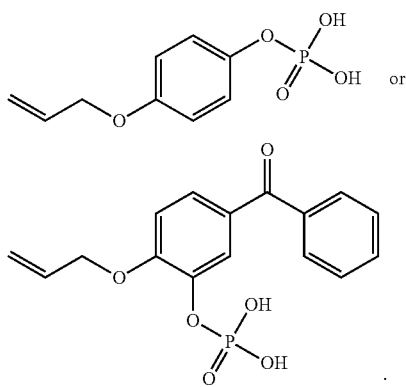

5. The composition according to claim 1, wherein polymerizable acidic phosphoric acid ester monomer of component (i) is characterized by one of the following formulas:

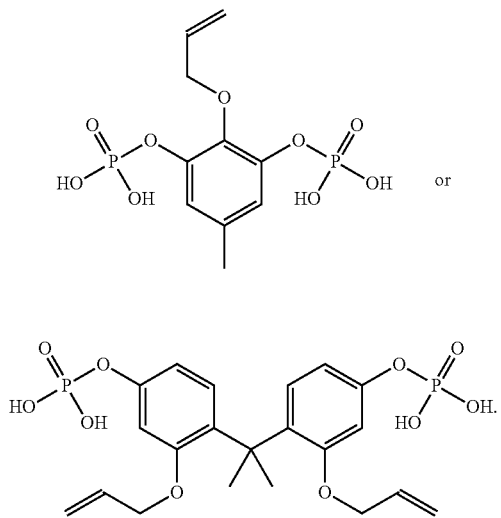

6. The composition according to claim 1, which further contains (viii) a polymerisable acidic monomer of the following formula (B):

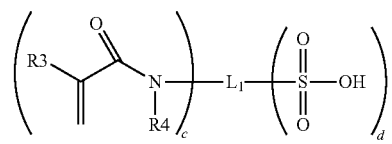

wherein
$R^3$ and $R^4$ independently represent
a hydrogen atom,
a $C_{1-16}$ alkyl group,
an optionally substituted $C_{3-8}$ cycloalkyl group,
an optionally substituted $C_{4-18}$ aryl or heteroaryl group,
an optionally substituted $C_{5-18}$ alkylaryl or alkylheteroaryl group, or
an optionally substituted $C_{7-30}$ aralkyl group,
whereby $R^3$ and $R^4$ may form together with the adjacent nitrogen and carbon atoms to which they are bound a 6- to 9-membered heterocyclic ring which may contain further nitrogen or oxygen atoms, and whereby the optionally substituted groups may be substituted by 1 to 5 $C_{1-5}$ alkyl group(s);
$L_1$ represents a (c+d) valent organic residue containing 2 to 45 carbon atoms and optionally oxygen, nitrogen and/or sulfur atoms, the carbon atoms including c+d carbon atoms selected from primary and secondary aliphatic carbon atoms, secondary alicyclic carbon atoms, and aromatic carbon atoms, each of said c+d carbon atoms linking a sulphonate or optionally substituted acrylamido derivative group; and
c and d independently represent an integer of from 1 to 10.

7. The composition according to claim 1, which is stable at storage for at least 10 days at 60° C.

8. The composition according to claim 1, which has a pH of at most 5.

9. The composition according to claim 1, which is a one part self-etching, self-priming dental adhesive.

10. The adhesive according to claim 6, wherein said acidic polymerizable monomer of formula (B) is characterized in that c is 1 or 2.

11. The adhesive according to claim 6, wherein said acidic polymerizable monomer of formula (B) is characterized in that d is 1 or 2.

12. The adhesive according to claim 6, wherein said acidic polymerizable monomer of formula (B) is characterized in that $R^3$ and $R^4$ independently represent a hydrogen atom or a $C_{1-6}$ alkyl group.

13. The adhesive according to claim 6, wherein said acidic polymerizable monomer of formula (B) is characterized in that $L_1$ represents a (c+d) valent saturated hydrocarbon residue containing 2 to 10 carbon atoms and optionally oxygen, nitrogen and/or sulfur atoms.

14. The dental adhesive according to claim 6, wherein said acidic polymerizable monomer of formula (B) is characterized by one of the following formulas:

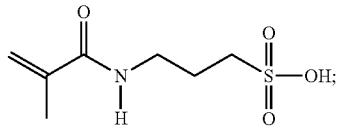

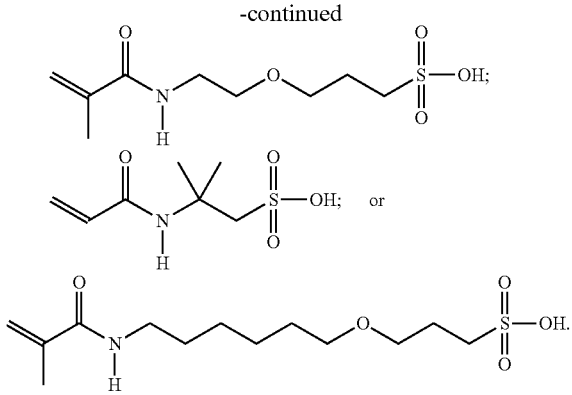

15. The composition according to claim 1, wherein the one or more polymerizable N-substituted alkyl acrylic or acrylic acid amide monomers of component (iii) are characterized by one of the following formulas:

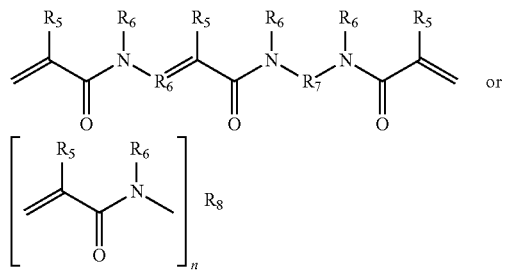

wherein $R_5$ and $R_6$ independently represent
- a hydrogen atom or a substituted
- a $C_1$ to $C_{18}$ alkyl group,
- an optionally substituted $C_{3-18}$ cycloalkyl group,
- an optionally substituted $C_{6-18}$ aryl or heteroaryl group,
- an optionally substituted $C_{6-18}$ alkylaryl or alkylheteroaryl group,
- an optionally substituted $C_{7-30}$ aralkyl group, $R_7$ represents
- a divalent substituted or unsubstituted organic residue having from 1 to 45 carbon atoms, whereby said organic residue may contain from 1 to 14 oxygen and/or nitrogen atoms and is selected from a $C_1$ to $C_{18}$ alkylene group wherein from 1 to 6 —$CH_2$— groups may be replaced by a —N—(C═O)—$CR_9$═$CH_2$ group wherein $R_9$ is a hydrogen atom or a $C_1$ to $C_{18}$ alkyl group, a divalent substituted or unsubstituted $C_3$ to $C_{18}$ cycloalkyl or cycloalkylene group, a divalent substituted or unsubstituted $C_4$ to $C_{18}$ aryl or heteroaryl group, a divalent substituted or unsubstituted $C_5$ to $C_{18}$ alkylaryl or alkylheteroaryl group, a divalent substituted or unsubstituted $C_7$ to $C_{30}$ aralkyl group, and a divalent substituted or unsubstituted $C_2$ to $C_{45}$ mono-, di- or polyether group having from 1 to 14 oxygen atoms, $R_8$ represents
- a saturated di- or multivalent substituted or unsubstituted $C_2$ to $C_{18}$ hydrocarbon group, a saturated di- or multivalent substituted or unsubstituted cyclic $C_3$ to $C_{18}$ hydrocarbon group, a di- or multivalent substituted or unsubstituted $C_4$ to $C_{18}$ aryl or heteroaryl group, a di- or multivalent substituted or unsubstituted $C_5$ to $C_{18}$ alkylaryl or alkylheteroaryl group, a di- or multivalent substituted or unsubstituted $C_7$ to $C_{30}$ aralkyl group, or a di- or multivalent substituted or unsubstituted $C_2$ to $C_{45}$ mono-, di-, or polyether residue having from 1 to 14 oxygen atoms, and n is an integer.

16. The composition according to claim 1, which contains the polymerizable acidic phosphoric acid ester monomer in an amount of from 0.5 to 20 wt-%.

17. The composition according to claim 6, which contains the polymerisable acidic monomer of formula (B) in an amount of from 0.5 to 20 wt-%.

18. The composition according to claim 1, which contains the one or more polymerizable N-substituted alkyl acrylic or acrylic acid amide monomers of component (iii) in an amount of from 10 to 70 wt-%.

19. The composition according to claim 1, wherein said polymerization initiator is a photo initiator.

20. The composition according to claim 5, which provides an adhesion to enamel and dentin of at least 15 MPa.

21. The composition according to claim 1, which contains nanofiller.

22. A method of using a polymerizable acidic phosphoric acid ester monomer being characterized by one of the following formulas:

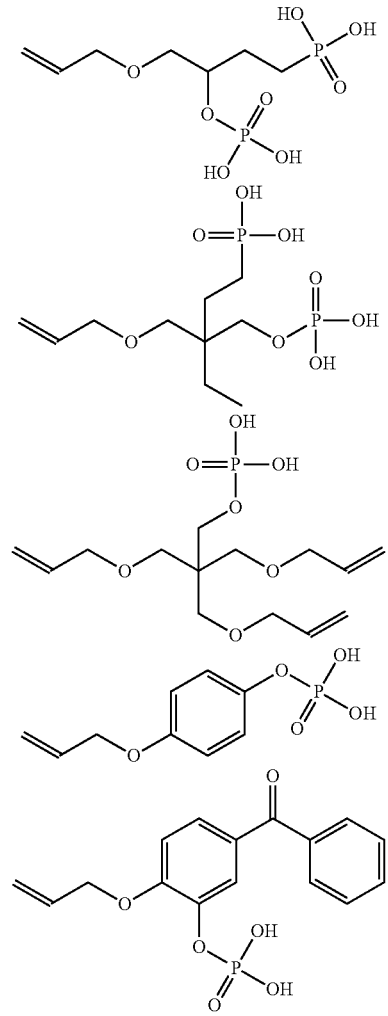

-continued
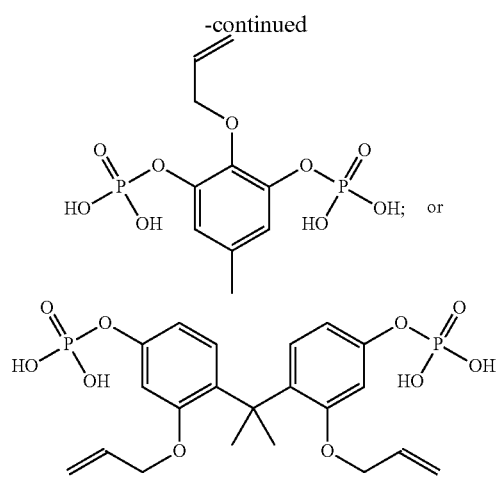
in an aqueous dental composition.
* * * * *